United States Patent

Chiba et al.

[11] Patent Number: 6,083,535
[45] Date of Patent: Jul. 4, 2000

[54] EFFERVESCENT GRANULAR PREPARATION FOR KEEPING CUT FLOWER FRESHNESS

[75] Inventors: Tadahiko Chiba, Saitama; Shiro Yamazaki; Toshihide Saishoji, both of Fukushima, all of Japan

[73] Assignee: Kureha Kagaku Kogyo K.K., Tokyo, Japan

[21] Appl. No.: 08/930,995

[22] PCT Filed: Feb. 27, 1996

[86] PCT No.: PCT/JP96/00445

§ 371 Date: Dec. 29, 1997

§ 102(e) Date: Dec. 29, 1997

[87] PCT Pub. No.: WO96/32012

PCT Pub. Date: Oct. 17, 1996

[30] Foreign Application Priority Data

Apr. 12, 1995 [JP] Japan ................................. 7-111233

[51] Int. Cl.⁷ ...................................................... A61K 9/14
[52] U.S. Cl. ........................ 424/489; 424/466; 424/464; 424/470
[58] Field of Search ................................... 424/464, 466, 424/488, 470, 489

[56] References Cited

FOREIGN PATENT DOCUMENTS

| 0 517212 A1 | 4/1992 | European Pat. Off. . |
|---|---|---|
| 3-163006 | 7/1991 | Japan . |
| 3-193703 | 8/1991 | Japan . |
| 4-117301 | 9/1992 | Japan . |
| 4-360802 | 12/1992 | Japan . |
| 5-255066 | 10/1993 | Japan . |
| 6-183903 | 7/1994 | Japan . |

*Primary Examiner*—Thurman K. Page
*Assistant Examiner*—William E. Benston, Jr.
*Attorney, Agent, or Firm*—McDermott, Will & Emery

[57] ABSTRACT

An effervescent granular preparation for keeping cut flower freshness includes an azole-substituted cyclopentanol derivative represented by formula (I) (set forth below) and 2-bromo-2-nitro-1, 3-propanediol as effective components and to a process for producing the same. The effervescent granular preparation is produced by granulation of a mixture containing at least one of glucose, D-mannitol and sucrose as an excipient by incorporating an organic acid such as citric acid or malic acid and a hydrogen carbonate such as sodium hydrogen carbonate.

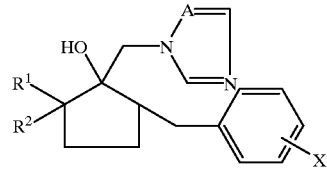

(I)

wherein A represents a nitrogen atom or a CH group, $R^1$ and $R^2$ represent each independently a hydrogen or a $C_1$–$C_3$ alkyl group, and X represents a hydrogen atom or a halogen atom.

13 Claims, No Drawings

EFFERVESCENT GRANULAR PREPARATION FOR KEEPING CUT FLOWER FRESHNESS

TECHNICAL FIELD

The present invention relates to a granular preparation for keeping cut flower freshness, and more particularly, to a novel effervescent granular preparation for keeping cut flower freshness, which can prevent the petals, stems, and leaves of cut flowers after the harvesting of flower and ornamental plants from wilting and can maintain color of petals and leaves for a long time, and a process for producing the same.

BACKGROUND ART

Tokkyo Kokai Hei 4-117301 discloses that a preparation comprising an azole-substituted cyclopentanol derivative represented by the following formula (I) (refer to as "compound (I)" hereinafter) as an effective agent has an effect of keeping the freshness by which the wilting of various kinds of cut flowers can be prevented to maintain their looks.

Tokkyo Kokai Hei 4-360802 discloses that the effect of keeping the freshness of cut flowers is further secured by using a compound represented by the following formula (I) together with 2-bromo-2-nitro-1,3-propanediol (refer to as "Bronopol" hereinafter).

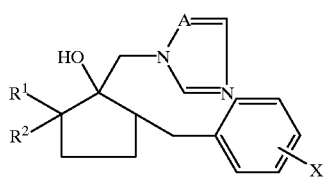

(I)

[In the formula (I), A represents nitrogen atom or CH group, $R^1$ and $R^2$ independently represent each hydrogen atom or a $C_1$–$C_3$ alkyl group, and X represents hydrogen atom or halogen atom.]

Concerning a preparation for keeping cut flower freshness which is applied by dissolving in water, it is important that the preparation is easily soluble in water and that the resulted solution is clear.

Since the above mentioned compound (I) is bad soluble in water, it is very difficult to prepare a liquid preparation having a uniform concentration by dispersing the solid type preparation such as powder, tablets or granules etc. which is the form usually used in the preparation for keeping cut flower freshness.

Addition of an assistant for dispersion has a drawback that it causes damaging the effect of keeping the freshness of cut flowers or reduction of the appreciative value of cut flowers because of causing spotted leaves.

On the other hand, a solution type preparation such as water solubilizing agent or emulsion etc., used for keeping freshness of cut flowers has been recognized to have a drawback of causing reduction of the effect of keeping freshness of cut flowers during preservation.

It has therefore been a need for developing a solid type preparation which has both the dispersibility-solubility in water and preservation stability for a long period of time.

Accordingly, an object of the present invention is to provide a solid type preparation comprising the above mentioned compound (I) and Bronopol as effective ingredients, which has the same effect of keeping freshness of cut flowers and the same dispersibility and solubility in water as those of the solution-type preparation for keeping cut flower freshness, and also has stabilized preservability for a long period of time.

DISCLOSURE OF THE INVENTION

The present inventors have made serious studies on the preparation for keeping cut flower freshness comprising the above mentioned compound (I) and Bronopol as effective ingredients in order to produce a solid type preparation which has preservation stability for a long period of time, is easily dispersible or soluble in water and has the same effect as that of the solution type preparation.

As a result, it has been found that an effervescent granular preparation for keeping cut flower freshness comprising at least one of saccharides such as glucose, D-mannitol, sucrose, etc. and sugaralcohols as the excipient, an organic acid such as citric acid, malic acid, etc., and a hydrogencarbonate such as sodium hydrogencarbonate, etc. has good preservation stability for a long period of time, is easily dispersible or soluble in water and the same effect of keeping the freshness of cut flowers as that of the solution type preparation.

The present inventors have been further found, regarding a process for producing an effervescent granular preparation for keeping cut flowers freshness, that a process comprising uniformly blending raw materials of the preparation, kneading with alcohols and granulating the mixture by a suitable method, a process comprising spraying a solution of the compound (I) and Bronopol in alcohol on granules containing no effective ingredient, or a process for directly granulating in a dry state is useful.

The present invention has been completed on the basis of the above described knowledges.

In the following, the present invention will be explained in detail.

The effervescent granular preparation for keeping cut flower freshness according to the present invention is characterized by containing an azole-substituted cyclopentanol derivative represented by the following formula (I) (Compound (I)) and 2-bromo-2-nitro-1,3-propanediol (Bronopol) as effective components.

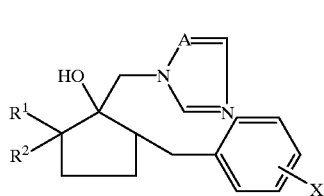

(I)

[In the formula (I), A represents nitrogen atom or CH group, $R^1$ and $R^2$ independently represent each hydrogen atom or $C_1$–$C_3$ alkyl group, and X represents hydrogen atom or halogen atom.]

The first aspect of the above-described effervescent granular preparation for keeping cut flower freshness according to the present invention is characterized by mixing at least one of water soluble saccharides or sugaralcohols exclusive of lactose, which has the water content of 2% or less, as an excipient.

The second aspect of the above-described effervescent granular preparation for keeping cut flower freshness according to the present invention is characterized by mixing at least one of glucose and D-mannitol, which has the water content of 2% or less, as an excipient.

The third aspect of the above-described effervescent granular preparation for keeping cut flower freshness according to the present invention is characterized by mixing an organic acid and a hydrogen carbonate as effervescing agents. More concrete, it is preferable to mix at least one organic acid selected from the group consisting of citric acid, succinic acid, malic acid, lactic acid, tartaric acid, fumaric acid and maleic acid, and one hydrogen carbonate selected from the group consisting of sodium hydrogen carbonate, potassium hydrogen carbonate and ammonium hydrogen carbonate.

The first process for producing the effervescent granular preparation for keeping cut flower freshness according to the present invention is characterized by carrying out granulation using alcohol as a solvent for granulation to obtain a granular product comprising the above described compound (I) and Bronopol as effective components.

In this process, ethanol or isopropanol is preferably used as the alcohol.

It is also preferred that the above described compound (I) is incorporated as a molecular dispersion.

The second process for producing the effervescent granular preparation for keeping cut flower freshness according to the present invention is characterized by carrying out granulation by a dry-type granulator to obtain a granular product comprising the above described compound (I) and Bronopol as effective components.

BEST MODE FOR CARRYING OUT THE INVENTION

The compound (I) which is one of the effective components in the present invention is the compound described in Tokkyo Kokai Sho 62-149667 and Tokkyo Kokai Hei 1-93574, in which the process for producing it is described.

Typical examples of the compound (I) used in the present invention are shown in Table 1.

In the "Expressions of stereoisomer" in Table 1, S and T show a stereostructure represented by the following formula (II) and a stereostructure represented by the following formula (III), respectively.

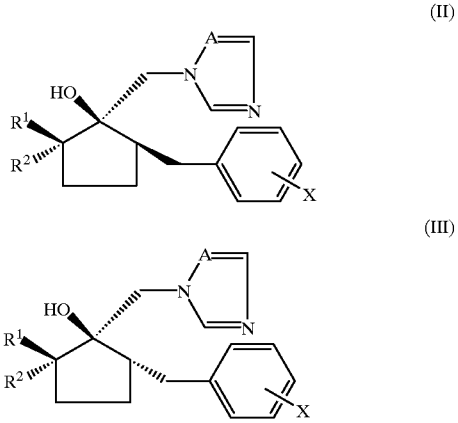

[wherein A, $R^1$, $R^2$, and X have the same meanings as the definition of the compound (II).]

TABLE 1

| Compound No. | Expression in formula (I) | | | | Expression of stereo-isomer |
|---|---|---|---|---|---|
| | $R^1$ | $R^2$ | X | A | |
| 1 | H | H | H | N | S |
| 2 | H | H | H | CH | S |
| 3 | H | H | 4-Cl | N | S |
| 4 | H | H | 4-Cl | CH | S |
| 5 | H | H | 4-F | N | S |
| 6 | H | H | 4-F | CH | S |
| 7 | H | H | 4-Br | N | S |
| 8 | H | H | 4-Br | CH | S |
| 9 | $CH_3$ | $CH_3$ | H | N | S |
| 10 | $CH_3$ | $CH_3$ | H | CH | S |
| 11 | $CH_3$ | $CH_3$ | 4-Cl | N | S |
| 12 | $CH_3$ | $CH_3$ | 4-Cl | N | T |
| 13 | $CH_3$ | $CH_3$ | 4-Cl | CH | S |
| 14 | $CH_3$ | $CH_3$ | 4-Cl | CH | T |
| 15 | $CH_3$ | $CH_3$ | 4-F | N | S |
| 16 | $CH_3$ | $CH_3$ | 4-F | N | T |
| 17 | $CH_3$ | $CH_3$ | 4-F | CH | S |
| 18 | $CH_3$ | $CH_3$ | 4-F | CH | T |
| 19 | $CH_3$ | $CH_3$ | 4-Br | N | S |
| 20 | $CH_3$ | $CH_3$ | 4-Br | N | T |
| 21 | $CH_3$ | $CH_3$ | 4-Br | CH | S |
| 22 | $CH_3$ | $CH_3$ | 4-B | CH | T |
| 23 | $CH_3$ | H | 4-Cl | N | S |
| 24 | $CH_3$ | H | 4-Cl | N | T |
| 25 | $CH_3$ | H | 4-Cl | CH | S |
| 26 | H | $CH_3$ | 4-Cl | N | S |
| 27 | H | $CH_3$ | 4-Cl | N | T |
| 28 | $C_2H_5$ | H | 4-Cl | N | S |
| 29 | $C_2H_5$ | H | 4-Cl | N | T |
| 30 | $C_2H_5$ | H | 4-Cl | CH | T |
| 31 | $C_2H_5$ | H | 4-F | N | S |
| 32 | $C_2H_5$ | H | 4-F | CH | S |
| 33 | $C_2H_5$ | H | 4-Br | N | S |
| 34 | $C_2H_5$ | H | 4-Br | CH | S |
| 35 | H | $C_2H_5$ | 4-Cl | N | S |
| 36 | H | $C_2H_5$ | 4-Cl | N | T |
| 37 | $C_2H_5$ | $C_2H_5$ | 4-Cl | N | S |
| 38 | $C_2H_5$ | $C_2H_5$ | 4-Cl | N | T |
| 39 | $C_2H_5$ | $C_2H_5$ | 4-Cl | CH | S |
| 40 | $C_2H_5$ | $C_2H_5$ | 4-Cl | CH | T |
| 41 | n-$C_3H_7$ | H | 4-Cl | N | S |
| 42 | n-$C_3H_7$ | H | 4-Cl | CH | S |
| 43 | H | n-$C_3H_7$ | 4-Cl | N | S |
| 44 | i-$C_3H_7$ | H | 4-Cl | N | S |
| 45 | i-$C_3H_7$ | H | 4-Cl | N | T |
| 46 | i-$C_3H_7$ | H | 4-Cl | CH | S |
| 47 | H | i-$C_3H_7$ | 4-Cl | N | S |
| 48 | H | i-$C_3H_7$ | 4-Cl | N | T |
| 49 | H | i-$C_3H_7$ | 4-Cl | CH | S |
| 50[1)] | $CH_3$ $C_2H_5$ | $C_2H_5$ $CH_3$ | 4-Cl 4-Cl | N N | S S |
| 51[1)] | $CH_3$ $C_2H_5$ | $CH_2H_5$ $CH_3$ | 4-Cl 4-Cl | N N | T T |
| 52[1)] | $CH_3$ $C_2H_5$ | $CH_2H_5$ $CH_3$ | 4-Cl 4-Cl | CH CH | T T |

[1)]Compound Nos. (50) to (52) are isomer mixtures concerning $R^1$ and $R^2$, respectively.

The compound (I) in the present invention can be used as a state of salt. The salt is not restricted if it is salt of inorganic acid and salt of organic acid. Examples include nontoxic salts of inorganic acid (hydrochloride, nitrate, sulfate, phosphate, carbonate) and nontoxic salts of organic acid (acetate, oxalate, citrate, maleate, tartarate).

The compound (I) in the present invention is preferably used in an amount of from 0.01% by weight to 5% by weight and particularly from 0.1% by weight to 0.5% by weight. It is because the effect is not sufficiently exhibited when the amount of the compound (I) is less than 0.01% by weight and it becomes difficult to completely disperse or dissolve in water when the amount is above 5% by weight.

The Bronopol in the present invention is preferably used in an amount of from 0.1% by weight to 10% by weight and particularly from 0.3% by weight to 3% by weight, based on the weight of the whole amount of the effervescent granular preparation for keeping cut flower freshness. It is because the effect is not sufficiently exhibited when the amount of the Bronopol is less than 0.1% by weight and it becomes difficult to completely disperse or dissolve in water when the amount is above 10% by weight.

As the excipient which is a base for the effervescent granular preparation for keeping cut flower freshness of the present invention, any water soluble saccharide and sugaralcohol exclusive of lactose may be used without restriction. For example, glucose, mannitol and sucrose are preferred to use. Lactose which is generally used as the excipient for granules is not preferred in the invention because it damages the effect of the compound (I) for keeping the freshness of cut flowers.

These saccharides or sugaralcohols may be used alone or as a mixture of two or more of them. Since these saccharides or sugaralcohols are used as the excipients for the effervescent granular preparation for keeping cut flower freshness, it is necessary to severely describe their water content. In general, the water content of these excipients is preferably 2% or less, more preferably 1.5% or less and particularly 1% or less, based on the whole weight.

As the efferverscent agent in the effervescent granular preparation for keeping cut flower freshness, it is preferred to use a combination of a hydrogen carbonate and an organic acid.

Examples of the hydrogen carbonate include sodium hydrogen carbonate, potassium hydrogen carbonate and ammonium hydrogen carbonate.

Examples of the organic acid include citric acid, succinic acid, malic acid, lactic acid, tartaric acid, fumaric acid and maleic acid, etc.

The organic acid is preferably used in an amount of 0.5% by weight to 20% by weight and, particularly, 1% by weight to 10% by weight based on the whole weight of the effervescent granular preparation for keeping cut flower freshness according to the present invention. The organic acid may be used alone or as a mixture of two or more of them. The hydrogencarbonate can be preferably used in an amount of 0.25 times to 2 times by molar ratio of the amount of the organic acid.

Into the effervescent granular preparation of the present invention, it is possible if necessary to add ingredients conventionally used for preservation of cut flowers. For example, (1) sodium hypochlorite, thiosulfate, etc. may be used jointly in order to prevent the staleness of the water in which cut portions of cut flowers are soaked, and rotting of cut portions and/or stems in their soaked forms; (2) fertilizer components (phosphates, nitrates, etc.) may be jointly used as the nutrition for cut flowers; and (3) benzyladenine, B-Nine, etc. may be used for suppressing the growth of cut flowers.

The effervescent granular preparation of the present invention prepared using the above mentioned ingredients as raw materials has an increased stability as compared with the prior water soluble preparations or emulsion preparations, the stability of which can be kept for 3 years under conventional conditions.

In order to produce the effervescent granular preparation comprising the compound (I) and Bronopol as the effective components, saccharides or sugaralcohols as the excipient, and organic acids and hydrogencarbonate as the efferverscing components, it is possible to use a conventional process for producing granules which does not use water. For example, it is possible to use an extrusion granulation process, a fluidized layer granulation process, an agitation granulation process, a high-speed agitation granulation process, a compression (dry) granulation process, and a crushing granulation process, etc.

The extrusion granulation process comprises homogeneously mixing the above described raw materials of the present invention as a powder state, kneading the resulting mixture with alcohol to form a wet lump, and extruding the wet lump by means of a mesh screen.

The fluidized layer granulation process comprises introducing the above described raw materials of the present invention into a fluidized bed granulating machine, fluidizing by means of a stream and spraying a binder dissolved in alcohol or a mixture of alcohol/dichloromethane to produce granules. The binder is not restricted, if it can dissolve in alcohol. It is preferred to use cellulose derivatives such as hydroxypropylcellulose, hydroxypropylmethylcellulose, hydroxypropylmethylcellulose phthalate and the like, and pobidone.

The agitation granulating process comprises homogeneously mixing the above described raw materials of the present invention as a powder state, granulating the mixture with adding alcohol and drying to produce granules.

The high-speed agitation granulation process comprises introducing the above described raw materials of the present invention into a high-speed agitation granulating machine, blending and stirring at a high speed to fluidize the mixture and granulating by addition of alcohol.

A suitable binder may be used in the agitation granulating process or the high-speed agitation granulating process.

The compression (dry) granulation process is carried out by means of a dry type granulating machine, which comprises molding a mixture of raw materials under a high pressure and crushing the mold into granules having a suitable size. The molding can be carried out by any of the method of using a roller compactor, the method of using a slug tabletting machine and the method of using a briketting machine in the present invention.

The crushing granulation process comprises making a wet mass of the above described raw materials with alcohol, followed by crushing to form granules.

The effervescent granular preparation of the present invention can be produced according to the above described conventional granulating processes. However, dispersibility in water is sometimes insufficient when granules are made by merely mixing the compound (I) with other ingredients or vehicles, because the compound (I) as the effective component is bad soluble in water. In order to dissolve such a problem, it is preferred to disperse in the granules the compound (I) as a molecular state.

In order to disperse in the granules the compound (I) as a molecular state, a solution of the compound (I) in alcohol is sprayed to the granules which are composed of ingredients excluding the compound (I). In such a case, it is preferred to add pobidone, macrogol, cellulose derivative, etc. as the binder, by which dispersion in a molecular state is easily carried out.

The effervescent granular preparation for keeping cut flower freshness prepared by the above described formulation and process is a novel preparation of keeping the freshness of cut flowers, which is easily dissolved and dispersed in water to exhibit the same effect as in the prior water solubilizing agent, and is rich in stability.

The effervescent granular preparation for keeping cut flower freshness according to the present invention is effective for various varieties of cut flowers. Examples of flowers to which a particularly good result is exhibited include gerbera, roses, bellflowers, carnations, chrysanthemums, lilies, turkish bellflowers, stocks, sunflowers, bouvaridia, asters, etc.

Regarding varieties of these flowers, the present invention is effective for various types of flower, for example, minimum, small, and large type roses, and standard, spray, Euro type carnations, etc. Consequently, the use of the effervescent granular preparation for keeping cut flower freshness according to the present invention should not be restricted to specific species or varieties of flowers.

The preparation of the present invention can be used in a wide period of time of from shipment stage to the stage where a consumer arranges the flowers.

EXAMPLES

The present invention will be described in greater detail by referring to Preparation Examples and Test Examples. These examples are, however, not intended to restrict the present invention as long as they deviate from the scope of the present invention. In the preparation examples, "part" means "part by weight"

Preparation Example 1
Preparation of Effervescent Granular Preparation for Keeping Cut Flower Freshness An small amount of ethanol was added to a mixture of 0.3 parts of the compound (Compound No. 44) shown in Table 1, 1.0 parts of Bronopol, 2.2 parts of citric acid, 2.2 parts of malic acid, 2.2 parts of sodium hydrogen carbonate, 4.4 parts of magnesium sulfate and 87.7 parts of glucose. After kneaded the mixture, it was granulated by an extrusion granulating machine.

Comparative Preparation Example 1
Preparation of Powdery Preparation

A powdery preparation was prepared by mixing 0.3 parts of the compound (Compound No. 44) shown in Table 1, 1.0 parts of Bronopol, 88.7 parts of glucose and 10 parts of citric acid.

Comparative Preparation Example 2
Preparation of Aqueous Solution (The same Aqueous Solution as that Described in Japanese Unexamined Patent Publication Hei 4-360802)

An aqueous solution was prepared by using 0.0015 parts of the compound (Compound No. 44) shown in Table 1, 0.005 parts of Bronopol, 0.75 parts of glucose, 0.05 parts of citric acid and the balance of water in an amount of being 100 parts.

Test Example 1
Test for Determining Dispersibility in Water of the Effervescent Granular Preparation for Keeping Cut Flower Freshness 20 g of the above effervescent granular preparation for keeping cut flower freshness obtained by the Preparation Example 1 was added in 200 ml of stationary water. After it is completely hydrated, the solution was stirred by means of a bamboo stick by moving towards the left direction 10 times and then towards the right direction 10 times. The content was poured on a 42 mesh screen and dryed, and weight of the resulted precipitate was measured. The dispersibility in water was shown as a percent dispersibility calculated by the following formula (A). The results were shown in Table 2. For comparison, the same test was carried out using 20 g of the powdery preparation of the Comparative Preparation Example 1. Percent dispersibility=(20−precipitate)/20×100

TABLE 2

| Test number | Preparation | Dispersibility in water (%) |
|---|---|---|
| 1–1 | Effervescent granular preparation for keeping cut flower freshness | 100 |
| 1–2 | Powdery Preparation of Comparative Preparation Example 1 | 98 |

Test Example 2
Test for Determining the Effect of the Effervescent Granular Preparation for Keeping Cut Flower Freshness Before and After Preservation for a Long Period of Time at Elevated Temperature The effervescent granular preparation for keeping cut flower freshness of the above described Preparation Example 1 was airtightly sealed and preserved at 40° C. for 6 months in a constant temperature box. 5 g of the effervescent granular preparation for keeping cut flower freshness before or after the lapse of 6 months was diluted 200 times with water to prepare a test solution.

500 ml of the test solution was charged in a 500 ml conical flask and three cut roses were arranged in the conical flask and kept at room temperature of 25° C.

Water was daily added in an amount of being consumed. Wilting of the petals and leaves was observed, and the day at which the worth of the flowers disappeared was found to decide the storage day. The results are given in Table 3.

As comparative tests, results obtained by using the aqueous solution of Comparative Preparation Example 2 and tap water were shown in the table.

TABLE 3

(Test for determining the effect of keeping cut flower freshness before and after preservation for a long period of time at elevated temperature)

| Test No. | Preparation | Preservation for long time at elevated temperature | Storage date of cut flowers Roses |
|---|---|---|---|
| 2–1 | Effervescent granular composition of Preparation Example 1 | | 16 |
| 2–2 | Aqueous solution of Comparative Example 2 | Before | 16 |
| 2–3 | (Tap water) | | 5 |
| 2–4 | Effervescent granular composition of Preparation Example 1 | | 14 |
| 2–5 | Aqueous solution of Comparative Example 2 | After | 6 |
| 2–6 | (Tap water) | | 5 |

Test Example 3
Test for Determining Effect of Preventing Contamination of Water for Arranging the Cut Flowers Before or After Preservation of the Effervescent Granular Preparation for Keeping Cut Flower Freshness for a Long Period of Time at Elevated Temperature The effervescent granular preparation for keeping cut flower freshness of the Preparation Example 1 was airtightly sealed and preserved at 40° C. for 6 months in a constant temperature box. 5 g of the effervescent granular preparation for keeping cut flower freshness before or after the lapse of 6 months was diluted 200 times with water to prepare a test solution.

150 ml of the test solution was charged in a 300 ml conical flask. After ten cut stems of rose having the length of 2–3 cm were put in the flask, a silicone plug was put into the opening of the flask. After a group consisting of three conical flasks was shaken at 28° C. for 3 days, absorbance was measured to determine contamination of water for arranging the cut flowers. The results were are in Table 4.

As comparative tests, results obtained using the aqueous solution of Comparative Preparation Example 2 and tap water were shown in the table.

TABLE 4

(Test for determining effect of preventing contamination of water for arranging the cut flowers before or after preservation for a long period of time at elevated temperature)

| Test No. | Preparation | Preservation for long time at elevated temperature | Absorbance (660nm × 10⁻³) |
| --- | --- | --- | --- |
| 3–1 | Effervescent granular composition of Preparation Example 1 | | 12 |
| 3–2 | Aqueous solution of Comparative Example 2 | Before | 16 |
| 3–3 | (Tap water) | | 38 |
| 3–4 | Effervescent granular composition of Preparation Example 1 | | 14 |
| 3–5 | Aqueous solution of Comparative Example 2 | After | 61 |
| 3–6 | (Tap water) | | 38 |

Industrial Applicability

According to the present invention, it becomes possible to provide the effervescent granular preparation for keeping cut flower freshness comprising the compound (I) and Bronopol as effective ingredients, which has the same effect of keeping freshness of cut flowers and the same dispersibility and solubility in water as those of the solution-type preparation for keeping cut flower freshness, and also has stabilized preservability for a long period of time.

We claim:

1. An effervescent granular preparation for keeping cut flower freshness which is essentially dry and which comprises:

an azole-substituted cyclopentanol derivative represented by the following formula (I)

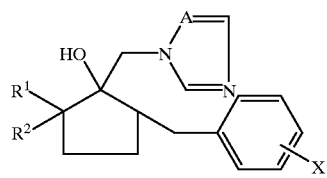

(I)

wherein,

A represents a nitrogen atom or a CH group, $R^1$ and $R^2$ independently represent each a hydrogen atom or a $C_1$–$C_3$ alkyl group, and X represents a hydrogen atom or a halogen atom, 2-bromo-2-nitrol-1, 3-propanediol as effective components, and an effervescing component which effervesces in the presence of water.

2. The effervescent granular preparation for keeping cut flower freshness according to claim 1, which further comprises at least one component selected from water soluble saccharides and sugaralcohols exclusive of lactose, which have a water content of 2% or less, as an excipient.

3. The effervescent granular preparation for keeping cut flower freshness according to claim 1, which further comprises at least one component selected from the group consisting of glucose, D-mannitol and sucrose, which have a water content of 2% or less, as an excipient.

4. The effervescent granular preparation for keeping cut flower freshness according to claim 1, wherein the effervescing component comprises a hydrogen carbonate and an organic acid.

5. The effervescent granular preparation for keeping cut flower freshness according to claim 1, which contains at least one organic acid selected from the group consisting citric acid, succinic acid, malic acid, lactic acid, tartaric acid, fumaric acid and maleic acid, and a hydrogencarbonate salt selected from the group consisting of sodium hydrogencarbonate, potassium hydrogencarbonate and ammonium hydrogencarbonate.

6. A process for producing an essentially non-aqueous effervescent granular preparation for keeping cut flower freshness comprising:

an azole-substituted cyclopentanol derivative represented by the following formula (I)

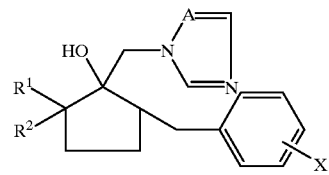

(I)

wherein,

A represents a nitrogen atom or a CH group, $R^1$ and $R^2$ independently represent each a hydrogen atom or a $C_1$–$C_3$ alkyl group, and X represents a hydrogen atom or a halogen atom, 2-bromo-2-nitro-1, 3-propanediol, and an effervescing component, and wherein:

the process comprises the step of carrying out granulation using alcohol as a solvent for granulation.

7. The process for producing the effervescent granular preparation for keeping cut flower freshness according to claim 6, wherein the alcohol is ethanol or propanol.

8. The process for producing the effervescent granular preparation for keeping cut flower freshness according to claim 6, comprising the step of using the azole-substituted cyclopentanol derivative represented by the above formula (I) as a molecular dispersion.

9. The process for producing the effervescent granular preparation for keeping cut flower freshness according to claim 8, comprising the step of using pobidone, macrogol or cellulose derivative as an assistant for forming the molecular dispersion.

10. A process for producing an effervescent granular preparation for keeping cut flower freshness comprising:

an azole-substituted cyclopentanol derivative represented by the following formula (I)

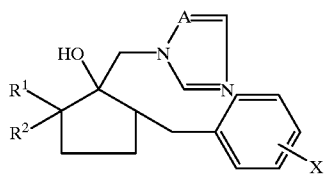
(I)

wherein,
- A represents nitrogen atom or CH group, R1 and R2 independently represent each hydrogen atom or C1–C3 alkyl group, and X represents hydrogen atom or halogen atom,
- 2-bromo-2-nitro-1, 3-propanediol as effective components,
- and which further comprises an effervescing component, and wherein the process comprises carrying out granulation by means of a dry type granulating machine.

11. An effervescent granular preparation for keeping cut flower freshness comprising:
- an azole-substituted cyclopentanel derivative;
- 2-bromo-2-nitrol-1, 3-propanediol, and
- a stable effervescing component which effervesces in the presence of water, and wherein said azole-substituted cyclopentanel derivative is represented by formula (I)

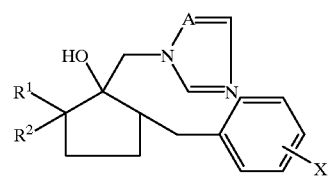
(I)

wherein,
- A represents a nitrogen atom or a CH group, $R^1$ and $R^2$ independently represent each a hydrogen atom or a $C_1$–$C_3$ alkyl group, and X represents a hydrogen atom or a halogen atom.

12. An effervescent granular preparation as set forth in claim 11, wherein said effervescing component comprises an organic acid and a hydrogencarbonate.

13. An effervescent granular preparation as set forth in claim 12, wherein granular compound further includes an excipient which contains 2% or less water and is selected from amongst the group comprising of glucose, D-mannitol and sucrose.

* * * * *